United States Patent [19]
Markoll

[11] Patent Number: 5,669,868
[45] Date of Patent: Sep. 23, 1997

[54] TREATMENT OF WRINKLED DISCOLORED OR AGING SKIN WITH MAGNETIC FIELD THERAPY

[75] Inventor: Richard Markoll, Middlebury, Conn.

[73] Assignee: Bio-Magnetic Therapy Systems, Boca Raton, Fla.

[21] Appl. No.: 625,089

[22] Filed: Mar. 22, 1996

Related U.S. Application Data

[63] Continuation of Ser. No. 471,853, Jun. 6, 1995, abandoned, which is a continuation of Ser. No. 162,694, Dec. 7, 1993, abandoned, which is a continuation-in-part of Ser. No. 867,362, Apr. 13, 1992, Pat. No. 5,387,176, which is a continuation-in-part of Ser. No. 519,410, May 4, 1990, Pat. No. 5,131,904.

[51] Int. Cl.$^6$ .................................................. A61N 1/00
[52] U.S. Cl. ......................................... 600/14; 600/15
[58] Field of Search ................................. 600/9–15

[56] References Cited

U.S. PATENT DOCUMENTS

| | | | |
|---|---|---|---|
| 3,915,151 | 10/1975 | Kraus | 600/13 |
| 4,428,366 | 1/1984 | Findl . | |
| 4,641,633 | 2/1987 | Delgado | 600/13 |
| 4,674,482 | 6/1987 | Waltonen . | |

FOREIGN PATENT DOCUMENTS

| | | | |
|---|---|---|---|
| 1150361 | 9/1980 | Canada . | |
| 2591495 | 6/1987 | France . | |
| 3246128 | 6/1983 | Germany | 600/13 |
| 3517874 | 5/1985 | Germany . | |
| 1639663 | 4/1988 | U.S.S.R. . | |

OTHER PUBLICATIONS

Jerome Faist, Federico Capasso, Deborah L. Sivco, Carlo Sirtori, Albert L. Hutchinson, Alfred Y. Cho, "Quantum Cascade Laser", Science, vol. 264, Apr. 22, 1994, pp. 553–556.

Jerome Faist, Federico Capasso, Carlo Sirtori, Deborah L. Sivco, Albert L. Hutchinson and Alfred Y. Cho, "Vertical Transition Quantum Cascade Laser with Bragg Confined Excited State", Appl. Phys. Lett. 66(5), Jan. 30, 1995, pp. 538–540.

*Primary Examiner*—John P. Lacyk
*Attorney, Agent, or Firm*—Dallett Hoopes

[57] ABSTRACT

Process involves treating skin by subjecting it to magnetic therapy by an annular coil energized by pulsed D.C. voltage having a rectangular wave from pulsing at the rate of 1–30 CPS, the coil producing a field of under 20 gauss.

3 Claims, 1 Drawing Sheet

TREATMENT OF WRINKLED DISCOLORED OR AGING SKIN WITH MAGNETIC FIELD THERAPY

REFERENCE TO RELATED APPLICATIONS

This is a continuation of application Ser. No. 08/471,853, filed Jun. 6, 1995 now abandoned, which is a continuation of application Ser. No. 08/162,694 filed Dec. 7, 1993 now abandoned, which is a continuation in part of application Ser. No. 07/867,362, filed Apr. 13, 1992, now patent 5,387, 176 which is a continuation in part of application Ser. No. 07/519,410 filed May 4, 1990, now U.S. Pat. No. 5,131,904 issued Jul. 21, 1992.

BACKGROUND OF THE INVENTION

1. Field of the Invention

This invention relates to the treatment with magnetic field therapy of disease including painful, degenerative, injurious or inflamatory conditions of the human musculoskeletal system or parts thereof. More specifically, this invention relates to the treatment of wrinkled, discolored or aging skin with magnetic field therapy.

2. Description of Related Art including Information Disclosed under §§1.97 to 1.99

It has been recognized in the prior art that the application of a magnetic field to diseased organs can in some way be beneficial. An example is disclosed in the Kraus U.S. Pat. No. 3,915,151 which discloses the idea of imparting a low frequency AC source to a wound toroid into which an ailing limb is inserted. The imparted voltage creates a changing magnetic field. This treatment is coupled in Kraus with a galvanic action by means of plates disposed on either sides of the limb.

A more recent patent, U.S. Pat. No. 4,537,181 to Shaloob et al, discloses treating a patient with a magnetic field created by rotating permanent magnets.

Other patents somewhat of interest to the present invention are U.S. Pat. No. 4,233,965 issued Nov. 18, 1980 and U.S. Pat. No. 4,758,429 issued Jul. 19, 1988.

SUMMARY OF THE INVENTION

Under the present invention the skin area to be treated is subjected to an electromagnetic field driven by a pure DC voltage having an abruptly rising and abruptly deteriorating wave form at the rate of 1–30 cycles per second. The field at the target organ is of low intensity, preferably under 20 gauss.

In the magnetic therapy treatment of arthritis, in accordance with the parent application. I have observed that patients having treatment for arthritis symptoms in their hands and other body parts have noticed that after therapy, the body part under treatment "looked younger". While during the treatment the primary attention was focused on the reduction of pain and improvement of ranges of motion, I also noted that wrinkled, discolored, blotchy pigmentation or unhealthy complexion of the skin which is unbecoming, disfiguring and undesirable was reduced.

Recent studies of the results of treatment with magnetic field therapy have confirmed that there is indeed a cosmetic improvement in wrinkled, discolored or aging skin. Here, again, the reasons for this improvement and the exact mechanism by which the treatment derives its efficiency are not known. One postulate is that the improvement is at least in part linked to the formation of collagen during magnetic therapy treatment.

The fact that pulsed magnetic field can stimulate collagen and proteoglycan synthesis by connective tissue cells has been established in several laboratories in this country and Europe, most notably at the Strangeways Research Laboratories at Cambridge University. Fibroblasts and chondroblasts from a variety of tissues and animal sources have shown this response in laboratory experiments. Other tissues have been studied in vitro, and an increase in messenger RNA and protein synthesis deomonstrated. The Department of Pathology of Columbia University, College of Physicians and Surgeons was primarily involved in this research although other centers have made similar studies with similar results. The apparatus described in itself has been shown to have such an effect in vitro on bovine chondroblasts and on human skin fibroblasts.

Specifically, the study of human skin fibroblasts has demonstrated an increase in net collagen synthesis of 60% after in vitro stimulation with the apparatus described for treatments when compared to controls kept in the same room but not so stimulated.

BRIEF DESCRIPTION OF THE DRAWINGS

Other features and objects of the invention will be clear from the following specification including the drawings, all of which disclose a non-limiting form of the invention. In the drawings.

DESCRIPTION OF THE PREFERRED EMBODIMENT

Figure 1:
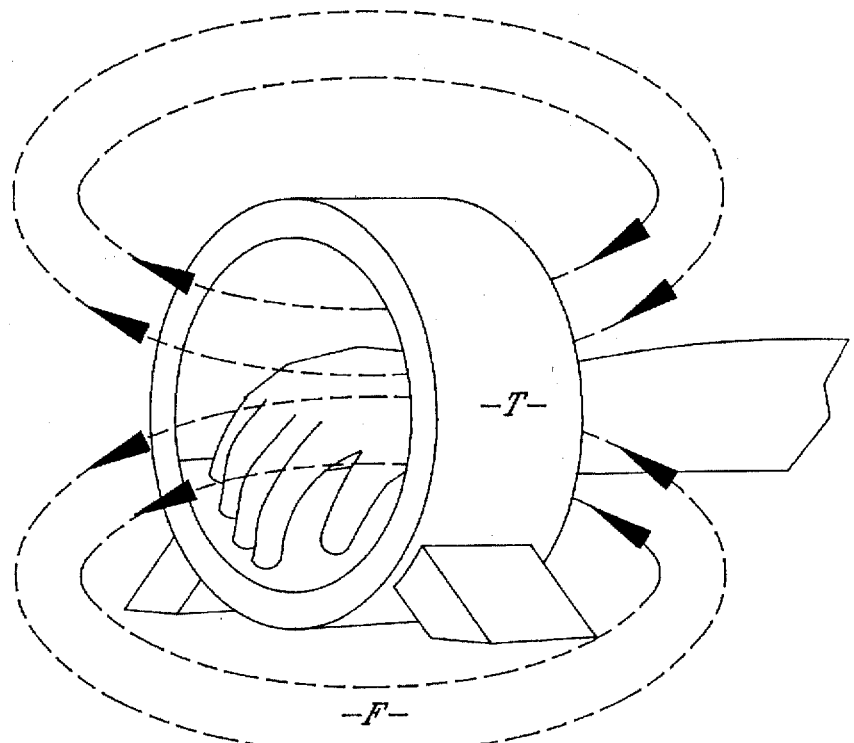
FIG. 1 is a simplified perspective view of a wound toroid energized to develop an electromagnetic field as indicated by flux lines, shown treating the skin of a human hand.
Figure 2:
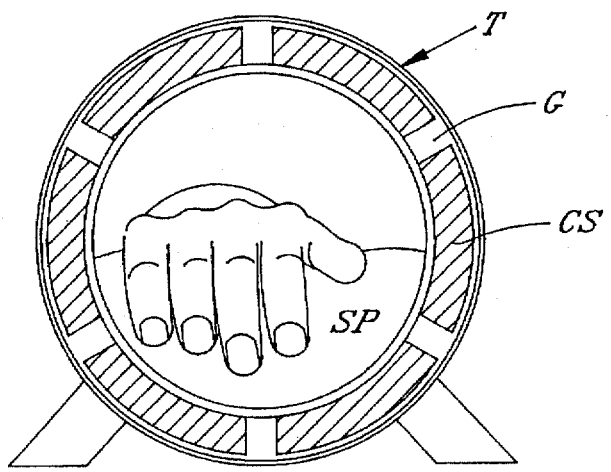
FIG. 2 is a front end view with front of cover removed and showing the coil setments inside the toroid.

Referring to FIG. 1 of the drawings, the invention involves the creation of an electromagnetic field F. This field is created by energizing a winding in a toroid I such that the field forms a three-dimensional donut in and about the toroid. The toroid I within its case contains a number of coil segments CS spaced by air gaps G as shown in FIG. 2. It is an important characteristic of the invention that the field not be greater than 20 gauss in the area of the diseased organ DO.

Figure 3:
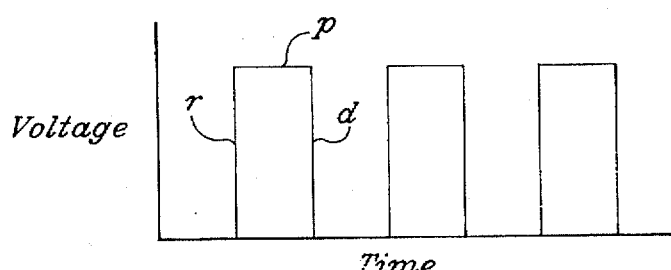
FIG. 3 is a graph showing the voltage flow vs. time as imparted to the toroid air coil to induce the magnetic field under the invention.

After much study, it has been found that it is important that voltage be supplied to the toroid winding in a pattern demonstrated in FIG. 3. The voltage supplied must repeatedly build up steeply, hold, and then deteriorate steeply and so that there are thus created a series of spaced working plateaus p of pure DC current. It is preferred, therefore, that in the duty cycle the wave form of the pure DC voltage involved be virtually of rectangular shape with the abruptly rising r and abruptly falling d sides of the wave form comprising sides of a rectangle. In between two such duty cycles there is an off cycle.

As an additional characteristic, further study has indicated that it is important that the movement of the field along the diseased limb, for instance, be toward its distal end. Thus, for instance, when treating a patient's hand as shown, or knee, as the diseased organ, the magnetic lines of the field F in the area of the organ should move toward the end of the appendage remote from the torso. This is achieved by supplying voltage of proper polarity to the coil leads of the toroid I.

As shown in FIG. 2, the target DO is supported to be in position eccentric to the central flux portion of the magnetic field within the toroid. This can be accomplished by a shapeable fiber support pillow SP of cotton or the like which need not completely surround the hand, for instance, but should assist its proper positioning. Inside the toroid housing, as stated, are a series of circularly arranged arcuate segments, of wound coil CS. With respect to the size of the toroid, I have found that for treatment of the hand a toroid having an opening of 5½" is preferable.

It has further been found that the length of time intervals between the treatment periods and the length of the treatment periods themselves is important. Preferably the length of sessions should be no greater than one-half hour and the frequency should be every 24 to 48 hours through the treatment period. A treatment period should be eighteen sessions.

Anecdotal patient date is persuasive of the usefulness of the treatment:

M., a 45 year old white female, and her daughter S., an 18 year old white female were involved in a motor vehicle accident mid-1992. M. and J. both suffered multiple injuries resulting in hematoma and ecchymotic discoloration of the thighs and lower limbs. During the 14 month period prior to entering the magnetic therapy program as described in this application in September 1993, both patients had discoloration of the thighs and lower limbs (ecchymoses) which remained unchanged and plainly obvious. After 18 treatments of the cervical spine and 18 treatments of the right knee and thigh, S. and the attending physician both noticed a significant reduction of the unwanted discoloration to a point that any dissimilarity to normal skin color was virtually indiscernible. M. received 18 treatments to the Thoracic Spine and 18 treatments to the Lumbar Spine. M and the attending physician both noticed a significant reduction of the unwanted discoloration to a point that any dissimilarity to normal skin color was virtually indiscernible.

B., a 78 year old white female, was prescribed large doses of prednisone (cortisone) over a 3 year period for a respiratory condition. The long term prednisone therapy resulted in severe thinning and atrophy of the skin on her hands and forearms. The patient complained of constant and repeated multiple severe injuries to the skin upon minimal frictional contact with clothing or during activities as simple as rubbing her hands or arms along a table top. These injuries were associated with multiple hemorrhages into the skin which resulted in unchanging discoloration. The attending physical and the patient's daughter, a Registered Nurse, noted multiple small eccyhmotic and hemorrhagic areas on her arms and hands. Wrinkling of large areas of the skin was moderately severe throughout the forearms and hands. There was obvious wasting of the skin. After a course of 18 treatments of magnatic therapy as described in this application, there was an obvious increase in skin thickness, turgor and an overall increase in the integrity of the skin tissue. The skin became more resistant to denuding, abrasion and tearing. The wrinkles were less obvious. Hemorrhages of the skin were less prevalent, and the skin was able to withstand greater stress. Improvement of the skin tone and color was apparent, compared to the untreated hand and forearm; this was authenticated by other attending physicians.

To demonstrate in a controlled experiment situation the unexpectable results of the invention, the following protocol was set up:

Five female subjects over 50 years of age and post menopausal who are in good general health, free of any dermatological disorders, with normal skin, and do not use treatment products on their hands were selected.

Clinical procedure:

The test sites are the back of the hands and the subjects agreed to refrain from using any treatment products on the test sites. They agreed to continue their normal routine and not change any of the soaps they use for the one-month study duration.

After skin evaluation the subjects reported for eighteen (18) one-half hour (0.5 hr) magnetic treatments over one month. One hand (randomly selected) was magnetically treated and the other served as its untreated control. After treatment the subjects were re-evaluated. The re-evaluation was a side-by-side comparison of the right vs. the left hand.

Instructions used for the Biophysical Skin Evaluation Procedures follow:

Skin Elasticity via Ballistometry

Skin elasticity will be assessed with the Ballistometer on the outer wrist area of both hands. The subjects will place their arms on a flat table surface, resting their hands on a sand bag. Skin elasticity will be assessed by dropping a very light weight (1–5 grams) pendulum on the skin surface and measuring the bounce of the pendulum via a computer.

Skin Moisturization via GBE

Skin moisturization will be assessed in the back of the hands with the Gas Bearing Electrodynamometer (GBE). The GBE accurately measures the force acting on the skin and the MM displacement of the skin due to that force. This displacement represents the strain of the hysteresis loop produced by the movement of the GBE probe, and the force applied is the stress of the hysteresis loop. The average slope of the hysteresis loop is proportional to 1/DSR (Dynamic Spring Rate) which is a measure of skin moisturization/softness.

Skin Barrier via Irans Epidermal Water Loss

Irans epidermal water loss (IEWL) will be evaluated with the Servo Med evaporimeter, fitted with a chimney and gauze. Water evaporation measurements will be taken at several different areas on the back of the hands, at baseline and after one month of treatment before and after hexana washing. The trans epidermal water loss will be recorded via a computer using the DIASIRON evaporimetry program.

Skin Desquamation and keratin analysis

Four D—Squames will be taken from each the right and left hands. The D—Squame discs will be mounted on clear microscope slides and labeled according to panelist name and visit. The samples will first be analyzed for the amount of desquamation via the Desquameter and then for keratin.

Skin surface patterns via Silicon Replicas and DIA

Silicon replicas of the skin surface patterns will be taken. A silicon replicating material (Silflow by Davis Inc. England) will be mixed with a catalyst and evenly spread on the back of each hand. As soon as they dry (1–2 minutes) they will be removed by gently pulling away from the skin in a downward direction. Two sets of replicas will be collected at each visit. The replicas will be labeled with the panelists name and visit. At the end of the study the replicas will be analyzed via digital image analysis for surface pattern morphology.

Skin Thickness and Density via ultrasound

Skin thickness and tissue density will be assessed with the ultrasound using a B scanning probe. Five ultrasound images on each test site will be stored in a computer to be analyzed via DIA for overall changes in skin density and skin thickness.

Skin Color

Skin color as well as dryness will be measured using the Minolta chromameter and Rainbow fiber optic microscope. A 2.5 cm diameter round glass cup will be placed on the back of the hand, one ml of cold (4 degrees C.) hexane will be pipetted into the cup, stirred with a glass rod for 30 seconds and removed by pipetting. The procedure will be performed on both hands. The hands will be allowed to air-dry for five minutes and measurements will be repeated.

Photo-documentation of skin changes

Close-up photographs will be taken using a Nikon camera with a Kiron 105 mm zoom lens fitted with a point flash at a fixed magnification. The subjects will position their hands on a hand rest the same way every time.

Clinical observation

These studies were commenced on one hand of five women, the other hand serving as control. The lab staff making the measurements were blinded as to which hand was treated.

The early results have been encouraging and initial data has led a major corporate firm to go forward with a significant amount of research, and do a large side study to obtain definitive data before proceeding to market testing.

"Discoloration" referred to herein may be either naturally occuring, such as age spots, or from disease traumatically induced, such as results from the consequences the various forms and manifestations of hematoma or ecchymosis, including discoloration caused by surgical (as in vein-stripping) or other intervention.

The invention may be defined as having the scope of the following claim language or reasonable equivalents thereof.

What is claimed is:

1. A process for treating wrinkled, discolored or aging skin in the absence of any electrical field and including the step of subjecting the skin to an electromagnetic field of under 20 Gauss generated by an annular coil into which the body part having the skin is placed, the coil being driven by a pulsed DC voltage having a rectangular wave form consisting of an abruptly rising and abruptly deteriorating current pulsing at the rate of 1–30 pulse bursts per second.

2. A treatment process as claimed in claim 1 wherein the electromagnetic field is about 12.5 gauss.

3. A treatment process as claimed in claim 1 wherein the treatment is performed for about 30 minutes every 24–48 hours during the course of treatment.

* * * * *